US012607628B2

(12) United States Patent
Wang et al.

(10) Patent No.: US 12,607,628 B2
(45) Date of Patent: Apr. 21, 2026

(54) APPARATUS FOR ACCELERATING UNIFORM REACTION OF REACTANTS WITH REACTANTS ON POROUS SUBSTRATE, SYSTEM CONTAINING THE APPARATUS, AND COATER

(71) Applicant: National Taiwan University, Taipei (TW)

(72) Inventors: An-Bang Wang, Taipei (TW); Chia-Chih Chu, Taipei (TW); Shih-Yi Chao, Taipei (TW); Hung-Nien Chiu, Taipei (TW); Chun-An Chen, Taipei (TW); Shih-Chung Chang, Taipei (TW); Jen-Ren Wang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 1241 days.

(21) Appl. No.: 16/994,246

(22) Filed: Aug. 14, 2020

(65) Prior Publication Data

US 2021/0025882 A1 Jan. 28, 2021

Related U.S. Application Data

(63) Continuation-in-part of application No. 15/602,136, filed on May 23, 2017, now Pat. No. 10,775,373.

(30) Foreign Application Priority Data

Dec. 1, 2016 (TW) .................................. 105139709

(51) Int. Cl.
*G01N 33/543* (2006.01)
(52) U.S. Cl.
CPC . *G01N 33/54366* (2013.01); *G01N 33/54393* (2013.01)

(58) Field of Classification Search
CPC ......... G01N 21/8483; G01N 33/54393; G01N 33/54366; G01N 21/8488; G01N 21/8494; B05C 5/027; B05C 5/0254; B05C 5/0216
See application file for complete search history.

(56) References Cited

U.S. PATENT DOCUMENTS 2,916,012 A * 12/1959 Hergenrother ........ H01J 9/2277
430/26
5,421,516 A * 6/1995 Saitou ..................... C23C 26/00
239/455

(Continued)

FOREIGN PATENT DOCUMENTS

JP 2005211767 A * 8/2005
KR 20160080452 A * 7/2016

OTHER PUBLICATIONS

Machine Translation of KR-20160080452-A (Year: 2016).*

(Continued)

*Primary Examiner* — Lessanework Seifu
(74) *Attorney, Agent, or Firm* — MUNCY, GEISSLER, OLDS & LOWE, P.C.

(57) ABSTRACT

The present invention relates to an equipment for enabling and accelerating uniform reaction between a to-be-reacted substance contained in a porous substrate and a reactant, and the equipment comprises: a machine body having a draining bottom plate on which the porous substrate can be placed; and a coating head which is provided above the machine body, can be moved horizontally along the porous substrate while maintaining a predetermined height, and has one or more slits, wherein each slit has an injection opening at one end and a liquid output opening at the other end.

12 Claims, 9 Drawing Sheets

(56) References Cited

U.S. PATENT DOCUMENTS

| | | | |
|---|---|---|---|
| 9,492,836 B2 | 11/2016 | Wang et al. | |
| 2003/0175827 A1 | 9/2003 | Stillman et al. | |
| 2005/0191420 A1* | 9/2005 | Miyakawa | B41J 2/1606 |
| | | | 118/301 |
| 2007/0110836 A1* | 5/2007 | Fork | B29C 48/71 |
| | | | 425/133.5 |
| 2010/0206306 A1* | 8/2010 | Feriani | A61M 15/0091 |
| | | | 222/52 |

OTHER PUBLICATIONS

Machine Translation of JP 2005211767 (Year: 2005).*
Yen et al., "Western Blotting by Thin-Film Direct Coating", Analytical Chemistry, 2014, vol. 86, pp. 5164-5170.
Liu, Chao-Yuan et al., "Easy and Fast Western Blotting by Thin-Film Direct Coating with Suction", American Chemical Society, Jun. 2, 2016, pp. 6349-6356.
Wang, An-Bang et al., "Miniaturization of Thin-Film Direct Coating Technology for New Biomedical Applications", 18th International Coating Science and Technology Symposium, Sep. 21, 2016.

\* cited by examiner

Conventional WB ($1^{st}$ Anti-GST : 2 µg ; $2^{nd}$ GAM : 0.2 µg)

| GST (µg) | 6 | 3 | 1.5 | 0.75 | 0.38 | 0.19 | 0.09 |

Present work ($1^{st}$ Anti-GST : 0.02 µg ; $2^{nd}$ GAM : 0.5 µg)

| GST (µg) | 6 | 3 | 1.5 | 0.75 | 0.38 | 0.19 | 0.09 |

1012

1011

1012

1011

1012

1011

APPARATUS FOR ACCELERATING UNIFORM REACTION OF REACTANTS WITH REACTANTS ON POROUS SUBSTRATE, SYSTEM CONTAINING THE APPARATUS, AND COATER

BACKGROUND OF THE INVENTION

1. Technical Field

The present invention relates to a method for the uniform reaction on the porous materials, particularly to a method for enhancement of the uniform reaction on the porous materials.

2. Description of Related Art

According to the estimation of Ministry of Economic Affairs, Taiwan, the annual market scale of the detection reagents in Taiwan is about US$100 million. The annual market scale of the in vitro detection reagents is over US$5,000 million in the world. If the relevant diagnostic detection reagents are included, the annual market scale has already been up to US$30,000 million. Wherein, the immune-detection reagents account for 25%, and the clinical chemistry detection reagents account for 16.5%. It reveals that the immune-detection reagents have already become the mainstream of the detection reagent market.

Wherein, in the market of the detection reagent, the need of application for the uniformly coated biochemical molecules on the test piece, membrane, chip, plastics, metal, filter paper, organic material, medical-grade product or the substance made by the other biochemical molecules etc. become more and more important. Especially, in the case of the biochemical molecules which are scarce or expensive with the high unit price, a key technology for quickly and uniformly coating the microscale biochemical molecules has become extremely important.

In the recent years, the biomedical detection carried out by the immunoreaction mechanism has already been widely applied in different fields, such as HIV immunodetection, Lyme disease detection, Hepatitis B virus detection, the tumor marker screening, the health examination, and the various regular blood and urine detections etc. However, when the protein or antigen is analyzed by the immunodetection with the needs of high-price antibodies and high-efficient enzyme catalysis, the detection process is commonly lengthy. Therefore, how to reduce the antibody consumption without sacrificing the signal intensity and also to save the reaction time has become the key issue to reach the fast precision immunodetection.

In the conventional Western blotting method, the membrane is put in a container containing the antibody, and the antibody reacts with the target protein mainly via the diffusion mechanism. The mechanism of the conventional Western blotting method is based on the antibody binding to the target protein, and then the enzyme is used to display the color of the combined antibody-target protein complex. The specific tissue or cell sample containing the target protein is analyzed and quantified through detecting the localization of the displayed color or the density of the displayed color area. In the conventional Western blotting method, the target protein is transferred onto a polyvinylidene fluoride (PVDF) membrane and immersed in an antibody solution container. To cover the antibody on the membrane evenly and to reach the result of binding the antibody to the target protein, the overnight reaction and/or with the shaking way are commonly used in the conventional Western blotting method. However, this conventional method has some drawbacks, such as the high cost of the excessive antibody consumption and long operation time.

To reduce the antibody consumption, the drop injection or the spot coating method has been used in the market. The biochemical molecules are coated on the carrier, such as the slice, membrane or chip etc., then the air dry or the oven dry is used. But the primary antibody cost and the operation time are still unable to meet the requirement of the fast reaction at user's end. Recently, a feasible approach is to take the advantage of microfluidic chip, such as the microchip electrophoresis etc., in which the antibody is driven by the voltage in the electrophoresis system, and then it is conjugated with target protein on the surface of porous membrane. Although this technology has the advantages of high sensitivity and high repeatability, but the high cost on chip fabrication has still limited its application.

In addition, by using high unit price of antibody to carry out the biochemical and immunological test, it should always be considered to minimize the amount of antibody to reduce the cost under the required accuracy, and to offer multichannel detecting technology synchronously, in order to meet the goal of cost reduction, high speed, high throughput and accuracy.

In order to save the antibody consumption and reduce the operation time, the brand new thin-film direct coating method is designed and developed here. The film is coated on the substrate by the principle of the relative motion between the fluid and the substrate applied. The suitable coating interval, the fluid flow rate and the coating speed can be controlled to obtain the desired uniform thin wet film accurately. The thickness of the film determines the material consumption, and the diffusion distance among the molecules can be shortened to increase the reaction efficiency. However, when the thickness of liquid film is reduced to a critical thickness, the ratio of the surface area and the volume of the liquid film will be increased. The liquid film tends to reduce the total surface area to reach the minimum surface energy, so that the film will break and shrink nonuniformly to cause the uneven concentration and fail the detection. This is the difficult point of the prior art which could be also prevented by the present invention. The purpose of the present invention is to effectively increase the detection efficiency and reduce the processing cost by the premise without sacrificing the signal-to-noise ratio and reliability. Up to now, there is no uniform coating method and the reaction technique of the biochemical molecules similar to the present invention.

BRIEF SUMMARY OF THE INVENTION

The present invention provides a method for accelerating the uniform reaction on the porous materials. After a to-be-reacted substance (such as target protein) is transferred onto or directly coated on the porous material (such as polyvinylidene difluoride, PVDF) which is subsequently placed on the platform of the machine, a small amount of reactant (such as antibody) is injected into a compact coating head. Then, all parameters are set on the machine. The coating head maintains a constant coating distance above the porous material and moves along the surface of the porous material. The reactant is distributed and diffused uniformly on the porous material by the coating head and the surface tension.

The present invention provides a method of uniformly coating a reactant film onto a to-be-reacted substance. The reaction collision probability is increased and the need of the reactant-dosage consumption is reduced by increasing the area-to-volume ratio at the reaction interface. The steps comprise the followings: providing a thin-film direct coating method and an adjustable coating width, and uniformly coating a reactant film on a to-be-reacted substance.

The present invention provides a uniform chemical reaction to enhance for uniformly coating a reactant film on a to-be-reacted substance that is on the porous materials, the steps comprise the followings: providing a thin-film coating method, a porous material, and a negative pressure vacuum apparatus. Wherein, the thin-film coating method comprises a coating head, which is for uniformly coating the reactant on a porous material. The suction direction of negative pressure vacuum apparatus is not parallel to the film coating direction. A forced convection is produced, that forces the reactant moving in the direction to the to-be-reacted substance, and then inhibit the reactant moving to other directions due to the diffusion mechanism and cause the local concentration of reactant being higher. When the interaction of the reactant and the to-be-reacted substance is increased, the signal-to-noise ratio can be increased.

Another objective of the present invention is to provide an equipment for enabling and accelerating uniform reaction between a to-be-reacted substance contained in a porous substrate and a reactant, and the equipment comprises a machine body and a coating head. The machine body has a draining bottom plate on which the porous substrate can be placed. The coating head is provided above the machine body, can be moved horizontally along the porous substrate while maintaining a predetermined height, and has one or more slits, wherein each slit has an injection opening at one end and a liquid output opening at the other end.

Furthermore, the equipment further comprises a negative pressure vacuum apparatus connected to the draining bottom plate in order to provide a negative pressure to the porous substrate.

Furthermore, the draining bottom plate is a porous or non-porous material, and microchannels are provided at a surface of the draining bottom plate when the draining bottom plate is the non-porous material.

Furthermore, the microchannels have a gradient in the channel depths.

Furthermore, the equipment further includes a vibrator provided under the draining bottom plate.

Furthermore, the equipment further includes a waste liquid storage tank provided between the draining bottom plate and the negative pressure vacuum apparatus.

Furthermore, the coating head is further connected directly to a washing liquid storage tank.

Furthermore, the slit has two opposite sides that are not parallel to each other.

Furthermore, at least one side of the draining bottom plate is provided with a coating preparation zone.

Still another objective of the present invention is to provide a system for labeling a to-be-reacted substance rapidly, and the system includes the equipment of the invention and an optical image capture and analysis module.

Furthermore, the optical image capture and analysis module includes a camera that may be a charge coupled device (CCD), a complementary metal-oxide semiconductor (CMOS), or other photosensitive component module.

Furthermore, the system includes a test strip that works with the system, and the test strip is with one or more target to-be-reacted substances pre-fixated thereon.

Furthermore, the system includes a non-transitory machine-readable medium that stores a program for interpreting a reaction result of the test strip, wherein the non-transitory machine-readable medium is any one, or a combination of at least two, selected from the group consisting of the following modules: an image interpretation module, a quantification module, a reference database module, and a comparison module. The image interpretation module is configured to interpret the image of the test strip after reaction. The quantification module serves to determine the amount of the target to-be-reacted substance(s) in the test strip. The reference database module stores detection patterns of the target to-be-reacted substance(s) in the test strip and the related clinical symptoms. The comparison module compares the image of the test strip against the detection patterns to determine the reaction result of the test strip.

The another objective of the present invention is to provide a coating head including one or more slits, wherein each slit has an injection opening at one end and a liquid output opening at the other end, and the injection opening is not necessary to be positioned at the center of geometric symmetry. In a preferred embodiment, each slit has two opposite sides that are not parallel to each other.

Comparing to the conventional techniques, the present invention has the following advantages:

The present invention provides a method for enhancement of the uniform reaction on the porous materials, which is a quick, miniaturized and uniform coating method to reach cost reduction, high-speed, mass production and precise products for the market requirements.

The present invention provides a method for enhancement of the uniform reaction on the porous materials. Comparing with the conventional Western blotting method, the invention needs only $\frac{1}{9}$ of processing time and $\frac{1}{100}$ of reagent dosage to reach the same detection signal strength.

The present invention provides a method for enhancement of the uniform reaction on the porous materials, which is a quick, miniaturized and uniform coating method, and can be widely applied in biochemistry and immunology etc. for the huge market requirements.

The present invention provides a coating head that can be designed to include one or more slits, and that allows a liquid to be distributed evenly to two opposite lateral sides as well as in a downward direction by way of capillary action and gravity, without additional driving power. When the coating head includes a plurality of slits, various reactants can be tested at the same time for their reaction, or lack of reaction, with the to-be-reacted substance adsorbed on a porous substrate, thereby increasing detection efficiency significantly.

The present invention provides a piece of equipment that is equipped with the coating head of the invention, that allows manually or electrically driven movement as needed, that can work with draining bottom plates of different materials, and that can be used together with a negative pressure vacuum apparatus and an additional vibrator to shorten the operation time required.

The system of the present invention is useful in one-stop rapid screening and image presentation and may serve as a high-precision high-efficiency biomedical detection system as opposed to those employing the conventional Western blotting method, whose multi-station operation is time-consuming and labor-intensive. In addition, as the system of the invention works with the test strip by the reference database module, which is in the non-transitory machine-readable medium and stores the related clinical symptoms corresponding to the detection patterns, the system can replace the existing rapid screening operations that determine whether a test subject is infected only by means of a single to-be-reacted substance. Therefore, the system of the invention can be used in various circumstances to provide useful disease detection information (i.e., a test subject's disease development condition and the corresponding clinical statistics) in a real-time and objective manner, thereby assisting medical professionals in giving proper diagnoses and treatments.

DETAILED DESCRIPTION OF THE INVENTION

Figure 1:
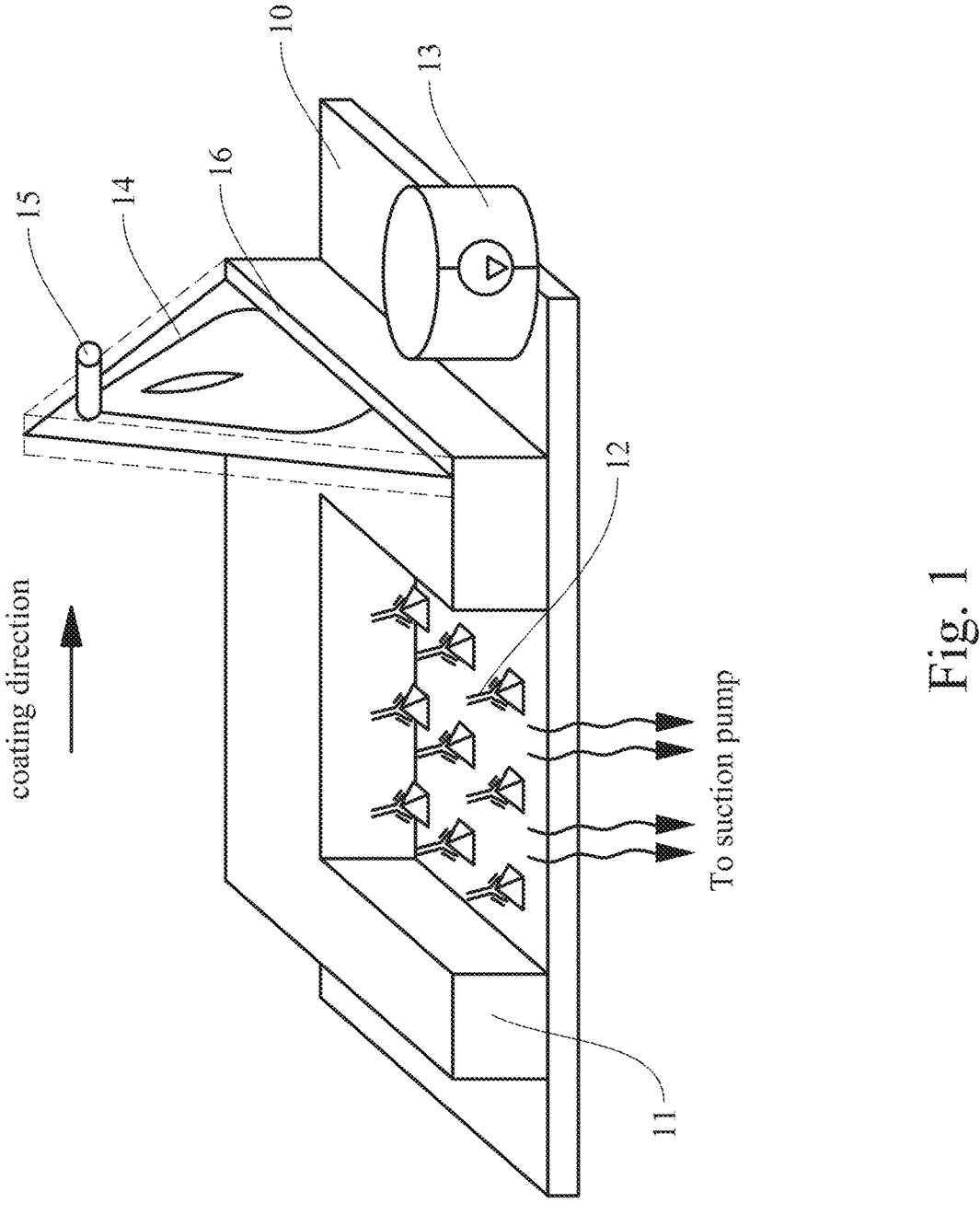
FIG. 1 illustrates an embodiment and method for enhancement of the uniform reaction on the porous materials in the present invention.

In the following description, the attached drawings will be used to describe the implementation of the present invention. In the drawings, the same symbol of element is used to represent the same element. Also, in order to explain clearly, the size or thickness of the element may be exaggerated.

As used herein, the terms "porous material", "porous-material substrate", "to-be-tested membrane", "membrane", and "porous substrate" refer to a membrane capable of adsorbing one or more to-be-reacted target substances in a biochemical reaction or immunoreaction, such as but not limited to a substrate membrane for use in the Western blotting method. The material of the membrane may be, but is not limited to, poly(vinylidene fluoride) (PVDF) or nitrocellulose (NC).

As used herein, the term "to-be-reacted substance" refers to the target substance (such as but not limited to an antibody or antigen) adsorbed or fixated on a porous substrate so as to react with the corresponding antigen or antibody or another chemical substance that can react with the target substance. The term "reactant" refers to a substance (such as but not limited to an antigen or antibody) with which a porous substrate is coated via the coating head, and that is intended to react with the target substance attached to the porous substrate.

As used herein, the terms "vacuum pump" and "negative pressure vacuum apparatus" refer to an apparatus capable of generating a negative pressure that in turn produces a suction force for drawing a liquid. As the direction of the suction force is not parallel to the coating direction of the coating head, forced convection takes place, and the reactant with which a porous substrate is coated is driven toward the to-be-reacted substance by the forced convection.

As shown in FIG. 1, an embodiment for a method for enhancement of the uniform reaction on the porous materials in the present invention is illustrated. After a to-be-reacted substance (such as target protein) is transferred onto or directly coated on a membrane 11 adsorbing a to-be-reacted substance, which is subsequently placed on the platform of the machine, a small amount (about $1/100$ of the amount used in the conventional Western blotting method) of reactant 12 (such as antibody) is injected into a light, compact and planar coating head 14. Then, all parameters could be set on the machine in order that the coating head 14 maintains a constant coating distance above the membrane 11 and moves along the surface of the membrane 11. The reactant 12 is distributed and diffused uniformly on the membrane 11 from the coating head 14 by the surface tension.

Figure 2:
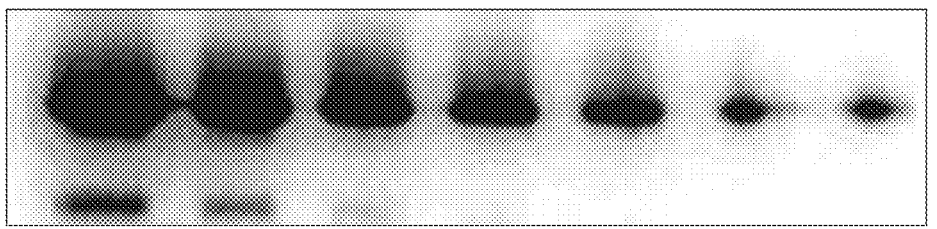
FIG. 2 illustrates the examples of experimental results for enhancement of the uniform reaction on the porous materials in the present invention.
Figure 2:
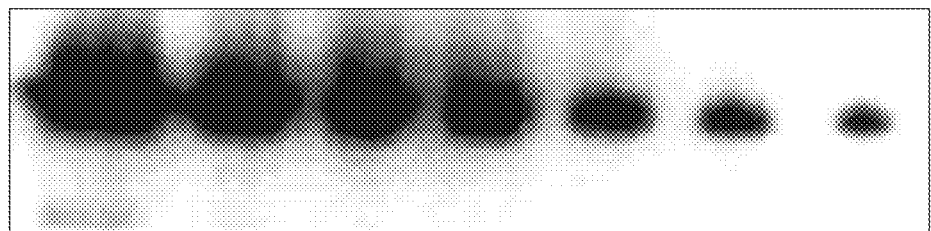

As shown in FIG. 2, the experimental results for the enhancement method of a uniform reaction on the porous materials in the present invention are illustrated. Except that reactant (such as antibody) consumption of the invention can be significantly reduced, it (such as antibody) can also contact the to-be-tested membrane (such as polyvinylidene difluoride, PVDF) uniformly, so that the antibody can effectively combine with the particular to-be-reacted substance (such as antigen), and increase the sensitivity of conventional Western blotting method.

A method for enhancement of the uniform reaction on the porous materials is described in the present invention. Firstly, a thin-film direct coating method is used to distribute the reactant (such as antibody) on the to-be-tested membrane (such as polyvinylidene difluoride, PVDF). The present invention collects the coating head, injection pump and/or surface tension as the fluid driving force. The reactant (such as antibody) is coated on the to-be-tested membrane (such as polyvinylidene difluoride, PVDF) which has the to-be-reacted substance (such as target protein).

A method for enhancement of the uniform reaction on the porous materials is described in the present invention. In the coating process, the speed of coating membrane, distance and the flow rate of transport fluid are controlled. The abovementioned speed of coating membrane, distance and the flow rate of transport fluid should be precisely matched, so that the reactant (such as antibody) will form a uniform and very thin liquid film after the coating is finished, and the combination time for the reactant probing with the to-be-reacted substance by the diffusion mechanism can be shortened. Because the film thickness of per unit area is positive proportional to the reactant amount of per unit area, that is, in the premise of the evenly liquid membrane, the reactant on every place of liquid membrane will be distributed uniformly to achieve uniform reaction.

A method for enhancement of the uniform reaction on the porous materials is described in the present invention, in which the vacuum is used to prevent the uneven concentration distribution for the diffusion of reactant (such as antibody). The reactant (such as antibody) contacting the to-be-tested membrane (such as polyvinylidene difluoride, PVDF)

which has the to-be-reacted substance (such as target protein) in the form of thin-liquid film is different from the diffusion phenomenon appeared when the antibody consumptions is getting much more as the prior art, where the ratio of the surface area to the volume for the film is increased, and the liquid film trends to reduce the overall surface area in order to reach the minimum low surface energy, that makes the film easy to be broken by shrinking and become the liquid pearl, and leads to the uneven concentration distribution.

A method for enhancement of the uniform reaction on the porous materials is described in the present invention, wherein the vacuum pump is used to force the convection of the reactant (such as antibody) by a negative pressure in order that the reaction time is further shortened and the noise signal caused by the non-specific combination is reduced. The invention uses a vacuum pump to force the reactant (such as antibody) moving to the to-be-reacted substance (such as target protein) by a negative pressure, and inhibit the reactant (such as antibody) moving to other directions due to diffusion mechanism that causes the local concentration of reactant being lower. Upon interaction of the reactant (such as antibody) and the to-be-reacted substance (such as target protein) is increased, the unreacted expensive antibody without combining with the target protein can be recovered and the signal-to-noise ratio can be increased. Through the automatic modularized, light, compact and thin coating head as well as the vacuum pump, the machine is already verified that the method of the invention can significantly reduce the antibody consumption and the operation time, reduce the human error, increase the detection efficiency, and sufficiently comply with the requirements of quick biomedical detection in the future.

The present invention for uniformly coating a reactant film on to-be-reacted substance by increasing the area-volume ratio of the reaction interface increases the reaction collision probability and reduces the whole reactant dosage. The method comprises the followings: providing a thin-film coating method and an adjustable coating width, and uniformly coating a reactant film on to-be-reacted substance.

The present invention provides a uniform chemical reaction to enhance for uniformly coating a reactant film on the porous materials. The steps comprise the followings: providing a thin-film coating method, a porous material substrate, and a negative pressure vacuum apparatus. The thin-film coating method comprises a coating head for uniformly coating the reactant on a porous material substrate. The suction direction of negative pressure vacuum apparatus is not parallel to the flat direction of the thin-film coating so that a forced convection is produced, forces the reactant moving toward to-be-reacted substance, and inhibits the reactant moving to other directions due to the diffusion mechanism that causes the local concentration of reactant being lower. When the interaction of reactant and to-be-reacted substance is increased, the signal-to-noise ratio can be increased.

The present invention has the quick detection function, because the premise is for reducing the detection time established under the same developing effect. This method uses the characteristics of the thin liquid film, which shortens the diffusion distance between the reactant (such as antibody) and to-be-reacted substance (such as target protein), and uses a vacuum pump to force the antibody moving to the target protein by controlling a negative pressure, in order to inhibit the reactant moving to other directions due to diffusion mechanism that causes the lower local concentration of reactant and also to increase the interaction of the antibody and the target protein to reach the quick reaction.

The antibody consumption of the conventional immunoreaction, such as Western blotting method, should be at least greater than 2 µg. In the embodiment of the present invention, the thin-film direct coating method is adopted, only 0.02 µg or even less of antibody is required to coat on the polyvinylidene fluoride membrane containing target protein, and as shown in FIG. 2, the content of target protein and the change of signal still can be detected stably and precisely; upon carrying out the high-price biochemical detection, the primary antibody cost can be lowered under $1/100$, which is significantly advanced compared with the existing technique.

The present invention provides a method for enhancement of the uniform reaction on the porous materials, which is the quick, miniaturized and uniform coating method to reach cost reduction, fast, high throughput and precise products for the market requirements. Also, comparing with Western blotting method, the present invention needs only $1/9$ of the processing time, and $1/100$ of the reactant dosage to reach the same detection signal strength. Summary by the abovementioned, the present invention provides a method for enhancement of the uniform reaction on the porous materials, which is a quick, miniaturized and uniform coating method, and can be widely applied in biochemistry and immunology etc. for the huge market requirements.

Figure 3:
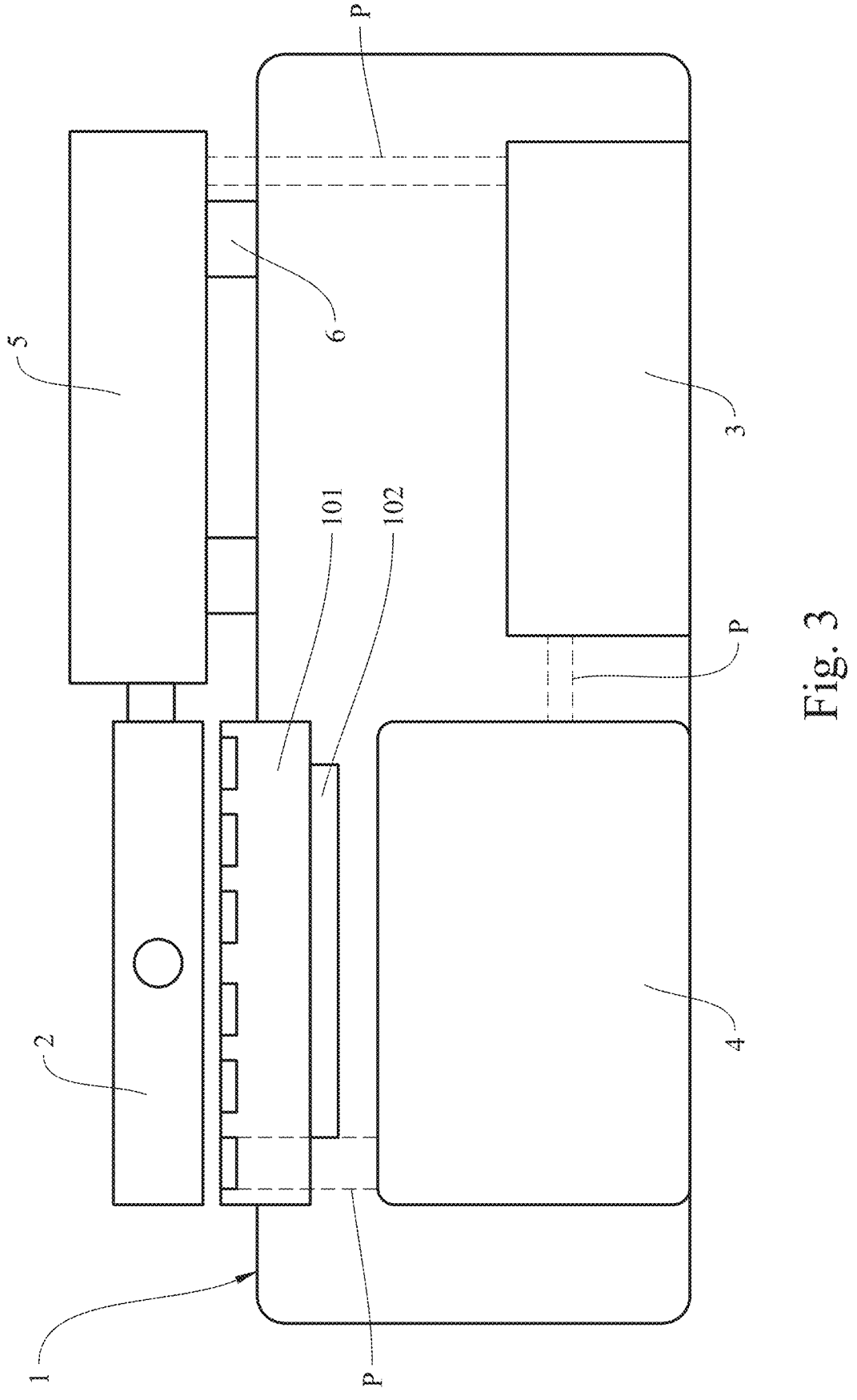
FIG. 3 shows a perspective view of the equipment of the present invention that is configured to enable and accelerate uniform reaction between a to-be-reacted target substance contained in a porous substrate and a reactant.
Figure 4:
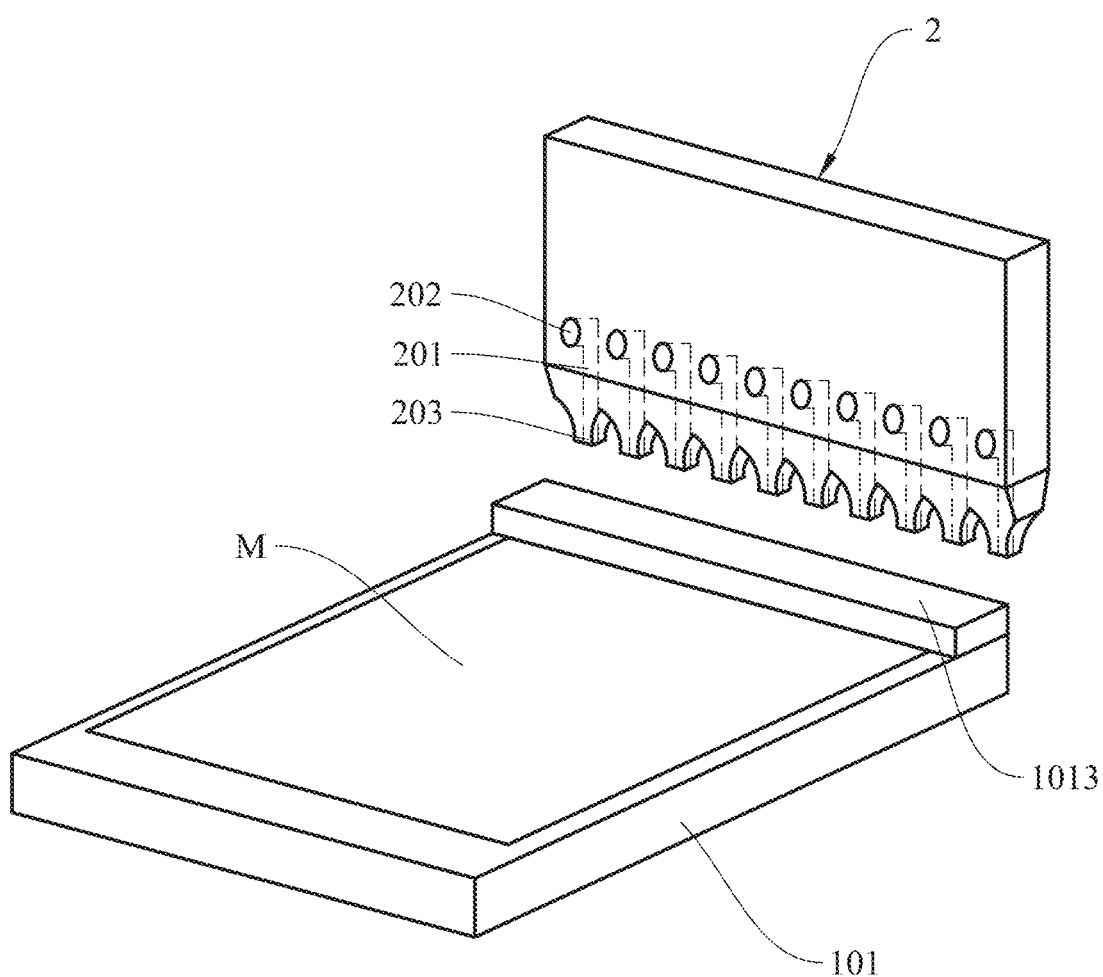
FIG. 4 shows a perspective view of the equipment of the present invention with a coating head and a draining bottom plate.
Figure 5:
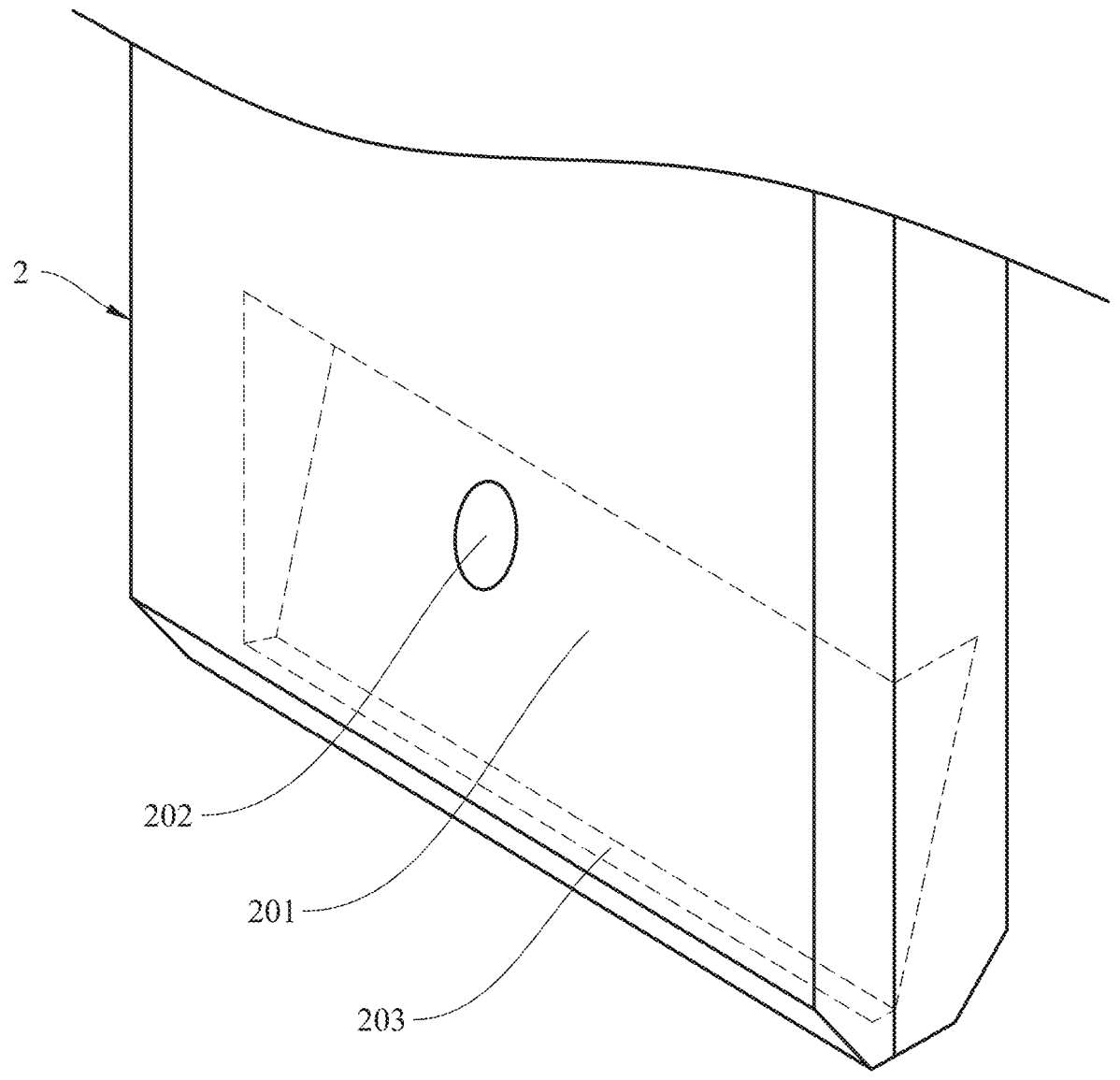
FIG. 5 shows a perspective view of the coating head of the equipment of the present invention.

FIG. 3 to FIG. 5 show the equipment according to an embodiment of the present invention that is configured to enable and accelerate uniform reaction between a to-be-reacted substance contained in a porous substrate and a reactant. The equipment includes a machine body 1, a coating head 2, and a negative pressure vacuum apparatus 3. The machine body 1 has a draining bottom plate 101 on which a porous substrate M can be placed. The coating head 2 is provided above the machine body 1 and can be moved horizontally along the porous substrate M while maintaining a predetermined height. The coating head 2 may have one or more slits 201. Each slit 201 has an injection opening 202 at one end and a liquid output opening 203 at the other end. Moreover, each slit 201 has two opposite sides that are not parallel to each other, as shown in FIG. 5. The negative pressure vacuum apparatus 3 is connected to the draining bottom plate 101 in order to provide a negative pressure to the porous substrate M.

When the equipment of the present invention is used for coating, a reactant may, as appropriate, be injected into the coating head 2 either manually (e.g., with a metering tool) or electrically (e.g., through an injection pump), such that the reactant enters the slits 201 through the injection openings 202. The reactant automatically forms a liquid bridge between the liquid output openings 203 and the porous substrate M by way of capillary action, gravity, and inertia. While the coating head 2 is horizontally moved, the liquid bridge of the reactant is laterally extended with a balance between the viscosity, capillarity, gravity, and inertia of the reactant, and coating is carried out as a result. It is generally believed that the coating head 2 must have flow guiding structures formed in two adjacent flat plates in order to guide the injected liquid downward, but the inventor of the present invention has found through experimentation that, as long as the coating head 2 has at least one slit 201 formed between two adjacent flat plates, preferably with the slit 201 having two opposite sides that are not parallel to each other, the injected liquid can be distributed evenly to two opposite lateral sides as well as in a downward direction by way of capillarity and gravity, without additional driving power (e.g., the driving power provided by an injection pump). The embodiment shown in FIG. 3 includes the negative pressure vacuum apparatus 3 to further shorten the reaction time and reduce noise resulting from non-specific binding. In another embodiment, however, the negative pressure vacuum apparatus 3, which is provided in a lower portion of the machine body 1, can be dispensed with as shown by experiment results, but the reactant in the coating head 2 will still be distributed evenly to two opposite lateral sides as well as in a downward direction by way of capillarity and gravity and then evenly over the porous substrate M, to which the to-be-reacted substance is adsorbed.

The coating head 2 may have one or multiple slits. The coating head 14 in FIG. 1 has only one slit, with an injection opening 15 above the slit and a liquid output opening 16 below the slit. It is not necessary to position the injection opening 15 at the center of geometric symmetry, nor is there any special limitation on the position of the injection opening 15. While the injection opening 15 in FIG. 1 is located in an upper surface portion of the coating head 14, it is feasible to position the injection opening 15 in a lateral portion of the coating head 14 instead, provided that the injection opening 15 allows a liquid to flow to the slit. The liquid output opening 16 forms an extensive opening below the slit of the coating head 14 so that the membrane 11 can be evenly coated with the reactant in the coating head 14. The coating head 2 in FIG. 4, on the other hand, has a plurality of slits 201. The slits 201 are independent of, and are not in communication with, one another. Each slit 201 has an injection opening 202 at an upper end and a liquid output opening 203 at a lower end. As the slits 201 are not in communication with one another, a different reactant can be injected into each injection opening 202, making it possible to test various reactants in a single test for their reaction, or lack of reaction, with the to-be-reacted substance adsorbed on the porous substrate M, thereby increasing detection efficiency significantly. The slits 201 in the present invention have a width of about 0.1-5 mm.

The equipment of the present invention is so designed that the coating head 2 can be horizontally moved in a manually driven or automatic manner. In the embodiment shown in FIG. 3, the equipment of the invention further includes a washing liquid storage tank 5. The coating head 2 is connected to the washing liquid storage tank 5 and can be horizontally moved via the slide rails 6 provided under the washing liquid storage tank 5. The driving force of the slide rails 6 may come from an electric motor or manual operation. The invention has no limitation on the location or driving method of the slide rails 6. A relatively simple and flexible way is to manually drive the coating head 2 into horizontal movement, and in that case, the electric motor for effecting horizontal displacement and the corresponding control system can be dispensed with to lower cost and enhance the convenience of operation.

In the equipment of the present invention, the draining bottom plate 101 is a substrate on which the porous substrate M can be placed. The draining bottom plate 101 may be a porous or non-porous material. If the draining bottom plate 101 is a porous material (e.g., foam, filter paper, or porous fiber, etc.), the pores of the draining bottom plate 101 will provide downward suction to draw the reactant containing liquid in the porous substrate M downward, thereby preventing the reactant from lateral dispersion, encouraging further dynamic reaction between the reactant and the to-be-reacted substance, and shortening the reaction time after coating. If the draining bottom plate 101 is a non-porous material such as glass, metal, poly(methyl methacrylate)

Figure 6:
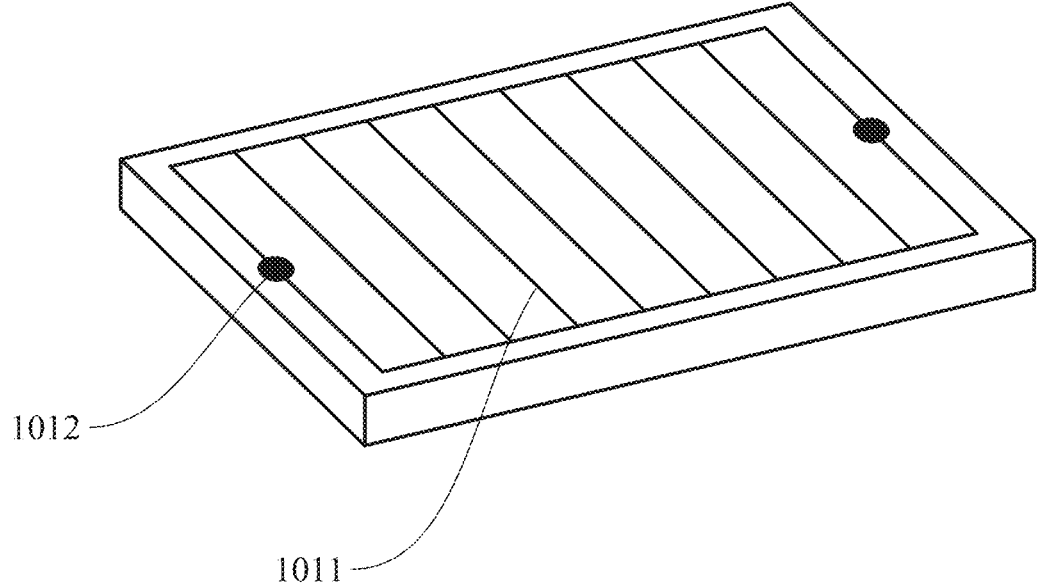
FIG. 6 shows a perspective view of a draining bottom plate (I) of the present invention that is made of non-porous material.
Figure 7:
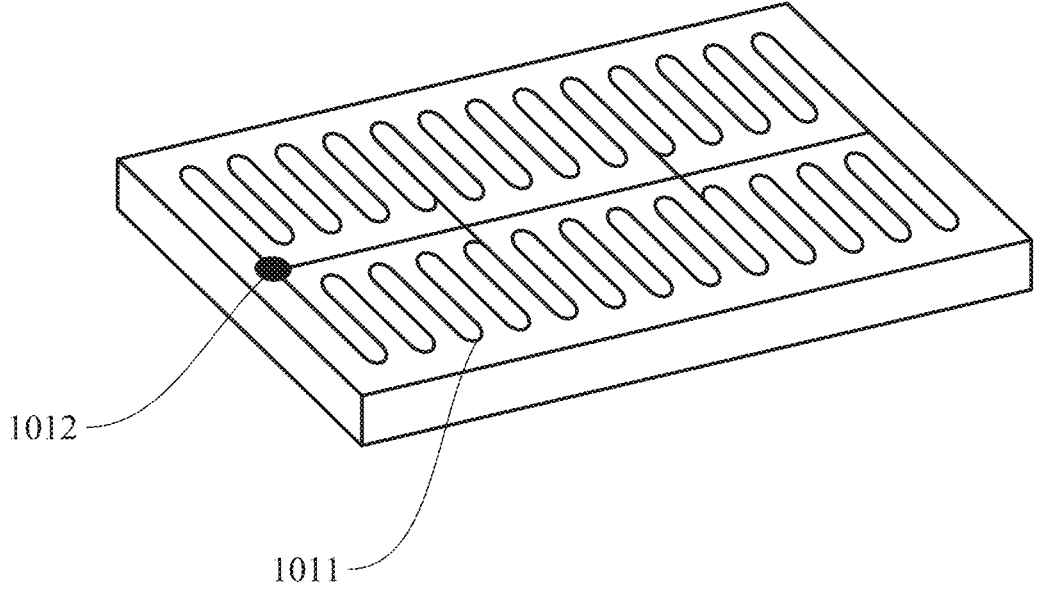
FIG. 7 shows a perspective view of a draining bottom plate (II) of the present invention that is made of non-porous material.
Figure 8:
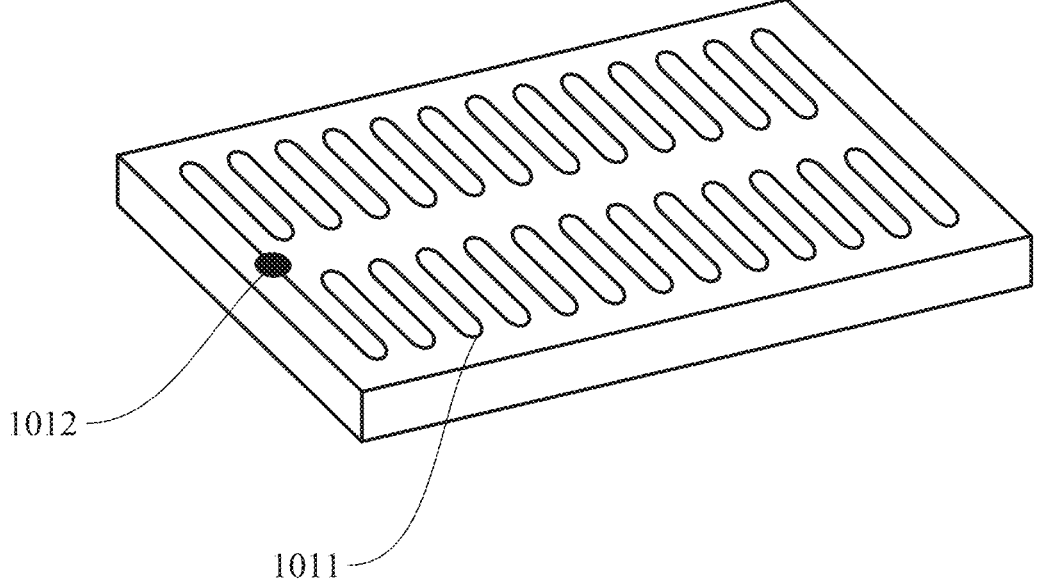
FIG. 8 shows a perspective view of a draining bottom plate (III) of the present invention that is made of non-porous material.

(PMMA, also known as acrylic), a polymer, silicone, plastic, or a combination of the above, etc., it is preferable that the draining bottom plate 101 has microchannels 1011 as shown in FIG. 6 to FIG. 8. The microchannels 1011 are thin, tiny structures that contribute to capillarity. Preferably, there is a gradient in the channel depths of the microchannels 1011 (i.e., the channel depths gradually increase or decrease), so the liquid in the microchannels 1011 will flow through capillarity caused by difference in elevation, with the relatively low channel sections provided at the end where a liquid outlet 1012 is located. The liquid outlet 1012 is configured for discharging a liquid, and there may be one or more liquid outlets 1012. In FIG. 6 for example, there are two liquid outlets 1012. In another embodiment, the liquid outlet 1012 is connected to the negative pressure vacuum apparatus. Preferably, the liquid outlet 1012 is provided in a portion of the microchannels 1011 that has a relatively great channel depth. Preferably, coating is carried out by the coating head 2 in a direction from a relatively shallow portion of the microchannels 1011 to a relatively deep portion of the microchannels 1011. Capillarity together with the depth difference of the microchannels 1011 enables the liquid in the microchannels 1011 to flow in a predetermined direction (i.e., toward the end where the liquid outlet 1012 is located). This flow design not only helps to collect the liquid flowing downwards, but also entrains the reactant containing liquid in the porous substrate M to be drawn downward. Furthermore, by combing the draining bottom plate 101 with the negative pressure, or suction power, generated by the negative pressure vacuum apparatus 3, the downward suction effect will be further enhanced to shorten the reaction time of the reactant and the to-be-reacted substance.

In one preferred embodiment, the draining bottom plate 101 is a non-porous material for the reasons stated below. When the draining bottom plate 101 is a porous material (e.g., foam, paper, porous fiber, or a metal mesh, etc.), the pores in the porous material provide suction power, so if the draining bottom plate 101 keeps absorbing liquid from the porous substrate M, the porous substrate M will be unable to stay moist to a certain degree. In other words, without proper and timely observation may lead to an inaccurate interpretation. Moreover, as residues of the reactant tend to be left in the pores of the porous material even after washing, it is impossible to use the porous material repeatedly. Having said that, a draining bottom plate 101 made of a porous material can still be used in a disposable manner in reactions for real time interpretation. By contrast, when the draining bottom plate 101 is a non-porous material as shown in FIG. 6 to FIG. 8, the capillary action in the microchannels 1011 and the channel depth gradient (or difference in elevation) enable the reactant containing liquid to flow to and discharge through the liquid outlet 1012, and the draining bottom plate 101, which has no pores, does not absorb the reactant containing liquid in the porous substrate M rapidly; as a result, the porous substrate M is kept from insufficient humidity (i.e., will stay in a state in which there is sufficient liquid in the porous substrate M and the liquid will not be drained too fast). In addition, a non-porous draining bottom plate 101 can be reused after washing. The material of the draining bottom plate 101, therefore, can be chosen to meet user needs, or the draining bottom plate 101 may be composed of detachable modules to facilitate installation and replacement. Besides, the draining bottom plate 101 may be further provided with a coating preparation zone 1013 as shown in FIG. 4 so that the coating head 2 can form a stable liquid bridge in the coating preparation zone 1013 before being horizontally moved over the porous substrate M to carry out the coating process. This allows a preset coating spacing to be maintained, lest the coating head 2 would be contaminated due to its directly contact with the porous substrate M. The coating preparation zone 1013 may be integrally formed with or additionally provided on the draining bottom plate 101.

Another embodiment of the equipment of the present invention further includes a vibrator 102 and a waste liquid storage tank 4. The vibrator 102 is provided under the draining bottom plate 101. The waste liquid storage tank 4 is provided, and is connected with pipes P, between the draining bottom plate 101 and the negative pressure vacuum apparatus 3. The washing liquid storage tank 5 is connected to the coating head 2, and the slide rails 6 are provided under the washing liquid storage tank 5.

The equipment according to the foregoing embodiment can be used to wash the porous substrate M. More specifically, when the intended reaction is completed, the porous substrate M can be coated with the washing liquid from the washing liquid storage tank 5 by the coating head 2, and the microchannels 1011 of the draining bottom plate 101 will keep the porous substrate M adequately wetted and full of washing liquid. In the meantime, the vibrator 102 will vibrate to wash excess reactant off the porous substrate M. In a conventional washing operation (e.g., the one employed in the Western blotting method) in the laboratory, the porous substrate M will have to be moved to and soaked in a washing liquid box, allowing spontaneous diffusion to take place under agitation for washing off the excess reactant. This process must be repeated several times to complete the washing and the entire washing operation is labor-intensive and time-consuming. By contrast, washing with the equipment of the present invention does not require the movement of the porous substrate M. This reduces the risk of damaging the porous substrate M while moving it. Also, the vibration-assisted washing process produces a superior washing result to that achievable by natural diffusion and agitation. Furthermore, when the draining bottom plate 101 is a non-porous material, the microchannels 1011 allow the pressure difference between the upstream and downstream ends of the porous substrate M to be evenly distributed during the liquid suction process so that effective and thorough cleaning can be attained with the smallest possible amount of washing liquid to shorten the operation time required.

Preferably, the vibrator 102 is an ultrasonic vibrator, is automatically activated in the washing process for the porous substrate M. Through the laterally back and forth relative motion of tens of thousands of times per second, the enhanced cleaning effect and significantly shorten the washing time can be achieved. The combination of the vibrator 102 and a non-porous draining bottom plate 101 is beneficial not only in washing the porous substrate M effectively within a short time, but also in suppressing the background noise in the detection signals so as to enhance system performance and signal clarity. Preferably, the equipment according to this embodiment of the present invention uses a non-porous draining bottom plate 101 and an ultrasonic vibrator 102 so that not only can finish effective washing within a short time, but also can effectively suppress the background noise during the signal detection to achieve better system performance and higher signal clarity.

Figure 9:
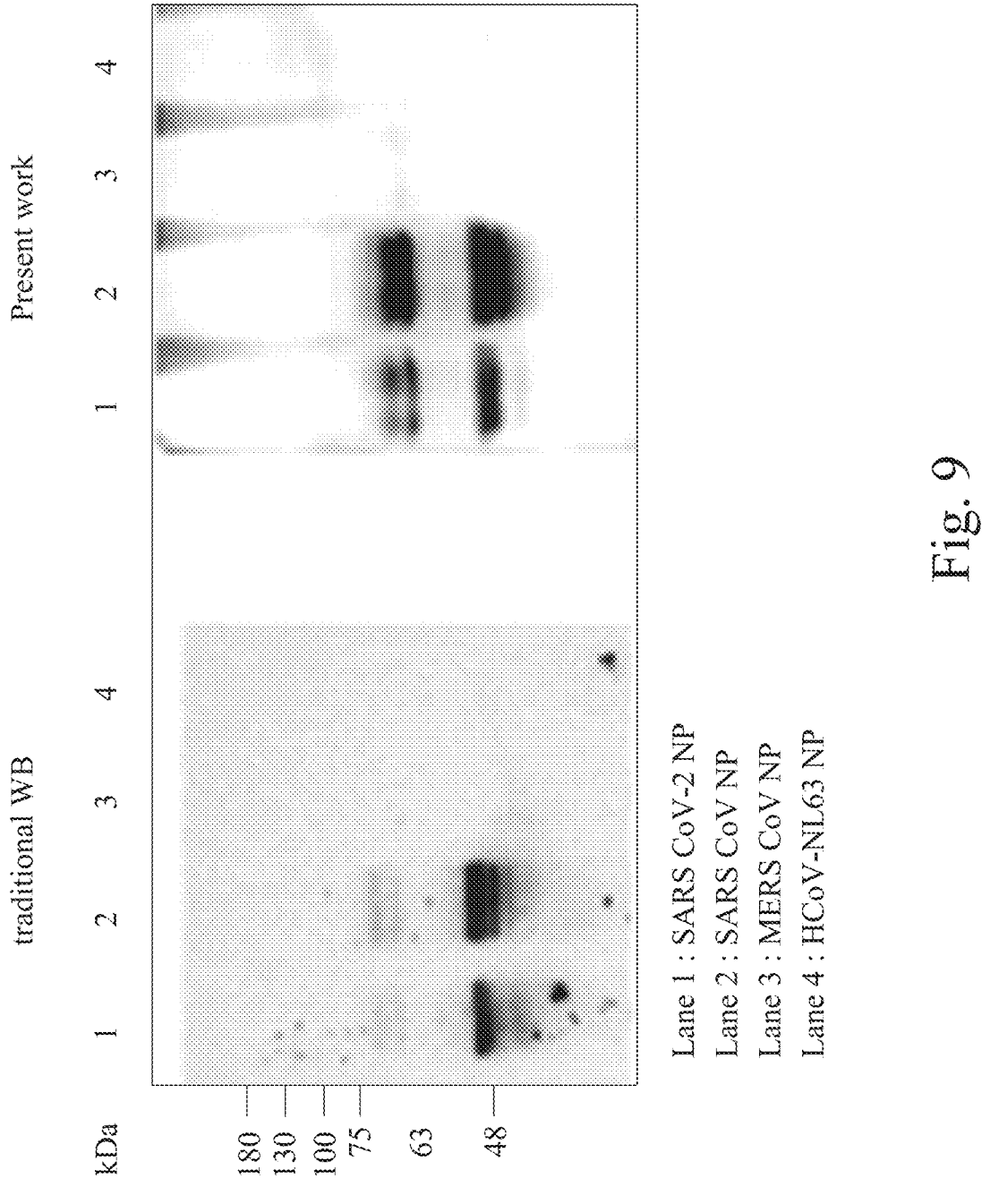
FIG. 9 shows the experiment results of Western blotting, wherein the right side shows the experiment result obtained with the equipment of the present invention, and the left side shows the experiment result of applying the conventional Western blotting method.

When Western blotting is performed with the equipment of the present invention, strong detection signals can be obtained. Referring to FIG. 9 for example, the left side of FIG. 9 shows the experimental result by applying the conventional Western blotting method while the right side shows the one obtained by the equipment of the invention. The four reactants under test being the nucleocapsid protein of a novel severe-acute-respiratory-syndrome coronavirus (SARS-CoV-2 NP), the nucleocapsid protein of a severe-acute-respiratory-syndrome coronavirus (SARS-CoV NP), the nucleocapsid protein of a Middle-East-respiratory-syndrome coronavirus (MERS-CoV NP), and the nucleocapsid protein of human coronavirus NL63 (HCoV-NL63). In contrast to the detection signals obtained with much more noise and relative weak signal by the conventional Western blotting method in the left figure, the detection signals obtained by the equipment of the invention are noise-free and clear in the right figure.

The present invention further provides a system for labeling a to-be-reacted substance rapidly. The system includes the foregoing equipment of the invention and an optical image capture and analysis module. The optical image capture and analysis module includes a camera for capturing, and presenting as an image, a detection result obtained with the equipment of the invention (e.g., by the Western blotting method). The optical image capture and analysis module may also include an excitation light source and a filter lens, and the image signals captured by the module may include cold light, ultraviolet (UV) light, fluorescent light, and visible light; the invention has no limitation in this regard. The system of the invention is useful in one-stop rapid screening and image presentation and may serve as a high-precision high-efficiency biomedical detection system as opposed to those employing the conventional Western blotting method, whose multi-station operation is time-consuming and labor-intensive.

The camera may be a charge coupled device (CCD), a complementary metal-oxide semiconductor (CMOS), or the like; the present invention has no limitation in this regard.

The system of the present invention may include and work with a test strip with one or more target to-be-reacted substances pre-fixated thereon, with the test strip serving as a porous substrate M for use with the equipment of the invention. Since one or more target to-be-reacted substances have been fixated on the test strip in advance, a sample with an unknown reactant can be rapidly tested and screened with the test strip. The test strip preferably has multiple target to-be-reacted substances pre-fixated thereon because the detection pattern (e.g., a band profile obtained with the Western blotting method) shown on a test strip with multiple to-be-reacted substances. This can replace those of conventional rapid test strips, which are based only on one to-be-reacted substance for determining whether the test subject is infected or not, by performance.

The system of the present invention may additionally include a non-transitory machine-readable medium that stores a program for interpreting the reaction result of the test strip. The non-transitory machine-readable medium may be any one, or a combination of at least two, selected from the group consisting of the following modules: an image interpretation module, a quantification module, a reference database module, and a comparison module. The image interpretation module and the quantification module are configured to interpret the image of the test strip after reaction. The quantification module serves to determine the amount of the target to-be-reacted substance(s) in the test strip. The reference database module stores detection patterns of the target to-be-reacted substance(s) in the test strip and the related clinical symptoms. The comparison module compares the image of the test strip against the detection patterns to determine the reaction result of the test strip. More specifically, test strips with different reactant detection patterns can be devised through molecular biological and serological designs and selections, and when a test strip has completed reaction through the equipment of the invention, the program in the non-transitory machine-readable medium can be used to interpret the reaction result, with the image interpretation module and the quantification module interpreting the image of the test strip, and the comparison module comparing the image against the detection patterns stored in the reference database module to produce the detection result. As the reference database module also stores the related clinical symptoms corresponding to the detection patterns, reference can be made to those clinical symptoms as well if the comparison shows a match between the image and one of the detection patterns. The system of the invention can thus replace those existing rapid screening operations that determine whether a test subject is infected only by means of a single to-be-reacted substance. The system of the invention can be used in various circumstances to provide useful disease detection information (i.e., a test subject's disease development condition and the corresponding clinical statistics) in a real-time and objective manner, thereby assisting medical professionals in giving proper diagnoses and treatments.

The above detailed description is a specific description of a feasible embodiment of the present invention, but the embodiment is not intended to limit the scope of the invention. Any equivalent implementation or change that does not depart from the technical spirit of the invention should be included in the scope of the invention.

What is claimed is:

1. A system for labeling a to-be-reacted substance rapidly, the system including:
an equipment for enabling and accelerating uniform reaction between the to-be-reacted substance contained in a porous substrate and a reactant, the equipment comprising:
a machine body having a draining bottom plate on which the porous substrate can be placed; and
a coating head provided above the machine body and can be moved horizontally along the porous substrate while maintaining a predetermined height, and the coating head has one or more slits, wherein each slit has a direct injection opening on the coating head; wherein liquid can be directly injected or filled into the slit through the direct injection opening from the outside of the coating head, and the liquid can be distributed in the slit by capillary, and the liquid can be discharged through the slit from output opening at a bottom of the coating head to the porous substrate by gravity and capillary without additional driving power; wherein the coating head is configured without external pipeline for feeding coating liquid; and
an optical image capture and analysis module.

2. The system of claim 1, wherein the equipment further comprises a negative pressure vacuum apparatus connected to the draining bottom plate in order to provide a negative pressure to the porous substrate.

3. The system of claim 1, wherein the draining bottom plate is a porous or non-porous material, and microchannels are provided at a surface of the draining bottom plate when the draining bottom plate is the non-porous material.

4. The system of claim 3, wherein the microchannels have a gradient in the channel depths.

5. The system of claim 4, further including a waste liquid storage tank provided between the draining bottom plate and a negative pressure vacuum apparatus.

6. The system of claim 5, further including a vibrator provided under the draining bottom plate.

7. The system of claim 6, wherein the coating head is further connected to a washing liquid storage tank.

8. The system equipment of claim 1, wherein at least one side of the draining bottom plate is provided with a coating preparation zone.

9. The system of claim 1, wherein each slit has two opposite sides that are not parallel to each other.

10. The system of claim 1, wherein the optical image capture and analysis module includes a camera.

11. The system of claim 10, further including a test strip that works with the system, and the test strip is with one or more target to-be-reacted substances pre-fixated thereon.

12. The system of claim 11, further including a non-transitory machine- readable medium that stores a program for interpreting a reaction result of the test strip, wherein the non-transitory machine-readable medium is any one, or a combination of at least two, selected from the group consisting of the following modules:
an image interpretation module for interpreting an image of the test strip after reaction; a quantification module serving to determine the amount of the target to-be-reacted
substance(s) in the test strip;
a reference database module storing detection patterns of the target to-be-reacted substance(s) in the test strip and related clinical symptoms; and
a comparison module for comparing the image of the test strip against the detection patterns to determine the reaction result of the test strip.

* * * * *